_ _

United States Patent [19]

Taicher et al.

[11] Patent Number: 6,069,479
[45] Date of Patent: May 30, 2000

[54] PERMANENT MAGNET MATERIAL COMPOSITION AND STRUCTURE FOR EDDY CURRENT SUPPRESSION IN A NUCLEAR MAGNETIC RESONANCE SENSING APPARATUS

[75] Inventors: Gersh (Zvi) Taicher; Arcady Reiderman, both of Houston, Tex.

[73] Assignee: Western Atlas International, Inc., Houston, Tex.

[21] Appl. No.: 08/959,766

[22] Filed: Oct. 29, 1997

Related U.S. Application Data

[63] Continuation-in-part of application No. 08/740,825, Nov. 4, 1996, abandoned.

[51] Int. Cl.$^7$ .................................................. G01L 3/00
[52] U.S. Cl. ......................... 324/309; 324/318; 324/321
[58] Field of Search ................................... 324/318, 319, 324/321, 322, 303

[56] References Cited

U.S. PATENT DOCUMENTS 5,621,324   4/1997   Ota et al. .................................. 324/319

FOREIGN PATENT DOCUMENTS 2 141 236   12/1984   United Kingdom .

OTHER PUBLICATIONS

Proceedings of the Fourth International Workshop on Rare Earth–Cobalt Permanent Magnets and their Applications, May 22–24 1979 Japan.

*Primary Examiner*—Christine K. Oda
*Assistant Examiner*—Brij B. Shrivastav
*Attorney, Agent, or Firm*—Richard A. Fagin; Madan, Mossman & Sriram

[57] ABSTRACT

A nuclear magnetic resonance well logging apparatus, comprising an antenna for inducing a radio frequency magnetic field in earth formations surrounding the apparatus and for detecting nuclear magnetic resonance signals from the earth formations; and a magnet for inducing a static magnetic field within the earth formations. The magnet is formed from a powdered, electrically conductive permanent magnet material. The grain size of the magnet material small enough with respect to the frequency of the radio frequency magnetic field to substantially prevent intragranular power loss of the radio frequency magnetic field. The magnet is formed from electrically isolated blocks of the magnet material each having a thickness less than a skin depth of the radio frequency magnetic field within the magnet material. The boundaries between the blocks are oriented to interrupt flow of eddy currents in the magnet resulting from the radio frequency magnetic field. In a preferred embodiment, the magnet material comprises powdered, epoxy resin-bonded Samarium-Cobalt.

24 Claims, 6 Drawing Sheets

PERMANENT MAGNET MATERIAL COMPOSITION AND STRUCTURE FOR EDDY CURRENT SUPPRESSION IN A NUCLEAR MAGNETIC RESONANCE SENSING APPARATUS

This is a continuation-in-part of Ser. No. 08/740,825 filed on Nov. 4, 1996.

BACKGROUND OF THE INVENTION

1. Field of the Invention

The invention is related to the field of electromagnetic well logging instruments and methods. More specifically, the invention is related to an apparatus and method for reducing the effect of eddy currents induced in a permanent magnet upon the measurements made by nuclear magnetic resonance ("NMR") well logging instruments.

2. Description of the Related Art

Electromagnetic well logging instruments include circuits connected to antennas which induce alternating electromagnetic fields in earth formations surrounding a wellbores, and include circuits which measure various electromagnetic phenomena which occur as a result of interaction of the alternating electromagnetic fields with the earth formations. Such electromagnetic phenomena relate to petrophysical properties of interest of the earth formations. One type of electromagnetic well logging instrument which suffers deleterious effects of eddy currents in electrically conductive elements of the logging instrument is the nuclear magnetic resonance ("NMR") instrument. One type of NMR instrument is described in U.S. Pat. No. 4,710,713 to Taicher et al. Another type of NMR instrument is described in U.S. Pat. No. 4,350,955 to Jackson et al. Both the Taicher et al '713 instrument and the Jackson et al '955 instrument include permanent magnets for inducing a static magnetic field in earth formations, and an antenna through which pulses of radio frequency ("RF") energy are conducted. RF energy conducted through the antenna induces an RF magnetic field in the wellbore, in any electrically conductive elements of the NMR instrument and in the earth formations surrounding the instrument. The RF energy passing through the antenna of the NMR instrument therefore causes eddy currents to flow in the wellbore, in the earth formation surrounding the NMR instrument and in any electrically conductive elements in the NMR tool.

In the Jackson et al '955 patent the antenna acts as a three-dimensional dipole. The direction of a magnetic field generated by the antenna is generally along the direction of the dipole and parallel to its longitudinal axis. This type of antenna is generally referred to as a longitudinal dipole. The antenna induces an RF magnetic field in the wellbore, in the earth formations surrounding the tool and in the permanent magnet material on both sides of the dipole along the longitudinal axis of the tool. To induce an RF magnetic field in the earth formations having sufficient amplitude to make useful NMR measurements, the antenna must also necessarily generate a relatively strong RF magnetic field within the permanent magnet. If the permanent magnet material is electrically conductive, losses of RF power will occur as a result.

The apparatus disclosed in the Taicher et al '713 patent includes a substantially cylindrical permanent magnet assembly which is magnetized perpendicular to its longitudinal axis. This magnet can be modeled as an infinitely long two-dimensional dipole. The magnet induces a static magnetic field in the wellbore and in the earth formations which has substantially uniform magnetic field strength within any thin annular cylindrical volume at a predetermined radial distance from the magnet. The Taicher et al '713 apparatus also includes an antenna, wound around the exterior of the magnet, for generating the RF magnetic field and for receiving NMR signals. This antenna can be modeled as an infinitely long two-dimensional dipole. The direction of the magnetic field generated by this antenna is generally perpendicular to its longitudinal axis. This type of antenna is referred to as a transversal dipole antenna. The permanent magnet's dipole is coaxial with and orthogonal to the RF magnetic dipole.

The apparatus disclosed in the Taicher et al '713 patent has several drawbacks. In particular, the antenna induces an RF magnetic field in the formations surrounding the tool which decreases in strength as the square of the radial distance from the magnet axis. Therefore, to induce an RF magnetic field in the earth formations having sufficient amplitude to make useful NMR measurements within a sensitive volume in the earth formations, the antenna must generate a very strong RF magnetic field, which is also very strong within the space that is occupied by the permanent magnet. If the magnet is made from electrically conductive permanent magnet material, significant losses of RF power will occur as a result of eddy currents flowing in the magnet. The apparatus disclosed in the Taicher et al '713 patent is generally useful only with an electrically non-conducting permanent magnet material such as ferrite.

Another NMR logging instrument is described in U.S. Pat. No. 5,055,787 to Kleinberg et al. This logging instrument includes permanent magnets arranged to induce a magnetic field in the earth formation having substantially zero field gradient within a predetermined sensitive volume. The magnets are arranged in a portion of the tool housing which is typically placed in contact with the wall of the wellbore. The antenna in the instrument described in the Kleinberg et al '787 patent is positioned in a recess located external to the tool housing, enabling the tool housing to be constructed of high strength material such as steel. This outside metallic structure also serves as a shield against RF alternating electromagnetic fields penetrating into the permanent magnet and resulting in RF power losses in the magnet.

Although instrument in the Kleinberg et al '787 patent reduces eddy current losses in electrically conductive elements of the tool by shielding the permanent magnet, this concept has several significant drawbacks. One such drawback is that the instrument's sensitive volume is only about 0.8 cm away from the tool surface and extends only to about 2.5 cm radially outward from the tool surface. Measurements made by this instrument tool are therefore subject to large error caused by roughness in the wall of the wellbore, deposits of the solid phase of the drilling mud (called "mudcake") onto the wall of the wellbore in any substantial thickness, and by the fluid content of the formation in the invaded zone.

Another way to reduce eddy current losses in the permanent magnet in an NMR logging apparatus is described in U.S. Pat. No. 5,376,884 and No. 5,486,761 to Sezginer. The instruments described in these patents use side-by-side spaced apart elongated magnets and an RF loop in the region between the magnets. Such an arrangement enables using relatively powerful permanent magnets, such as rare-earth magnets, provided that the permanent magnets are properly shielded. The basic disadvantage of the approach taken in the '884 and '761 patents is that the relatively large conducting surfaces will disturb the spatial distribution of the RF magnetic field while transmitting, and will reduce the signal to noise ratio ("S/N") while receiving NMR signals.

Finally, the signal to noise ratio of electromagnetic well logging instruments, particularly NMR tools, is generally greater at higher values of quality factor (Q) of the instrument's antenna. The relationship of the S/N with respect to the Q of the antenna is a primarily a matter of the particular instrument geometry. High magnitudes of eddy current loss restricts the Q of the antenna, thereby restricting the useful geometry of the logging instrument.

Generally speaking, the measurement approaches suggested in the Jackson et al '950 and the Taicher et al '713 patents are commercially preferred for making NMR measurements of earth formations. However, the apparatus described in both of these patents are preferably used with substantially non-conductive permanent magnets. Magnetic materials used to make permanent magnets generally fall into two classes: ferrites, which are oxides of ferromagnetic metals; and ferromagnetic metals and their alloys combined with other metals and/or rare earth elements. The first class generally consists of non-conductive permanent magnet materials, and the second class generally consists of electrically conductive materials. Both classes of permanent magnet materials can be used in making so-called "bonded" permanent magnets. Bonded permanent magnets are generally manufactured by pressure bonding or injection molding of magnet material powders in a carrier matrix. The carrier matrix is typically formed from an electrically non-conductive polymeric or epoxy resin. The magnet material density of this form of magnets is lower than magnets made entirely from sintered metallic materials, yielding lower magnetic strength properties in the final product. However, bonding or injection molding of permanent magnets often makes it possible to eliminate the need for costly secondary operations in the manufacturing process. See for example, "New Resin-Bonded Sm-Co Magnet Having High Energy Product (SAM)", Proceedings of the Fourth International Workshop on Rare Earth-Cobalt Permanent Magnets and Their Applications, Hakone National Park, Japan (1979).

The electrical resistivity of any particular bonded permanent magnet depends primarily on the resistivity of the magnet material powder, the proportion of the magnet material powder relative to the proportion of the carrier matrix in the finished magnet, and the particular manufacturing method which determines the degree of contact between the individual grains of the magnet material powders. While they are electrically non-conductive, ferrite magnet materials have low residual magnetization, generally about three times weaker than other magnet materials such as rare-earth Samarium-Cobalt, Alnico or Neodymium-Iron-Boron, all of which are very good electrical conductors. Ferrites are also about one and a half times weaker than some commercially available bonded rare-earth Samarium Cobalt or Neodymium-Iron-Boron magnets, which are considerably less conductive than sintered magnets made from the same materials. However, the particle size of the magnet material powders and material proportion, as well as the bonding process, generate significant eddy current losses within the conductive particles themselves and between them in the overall magnet structure.

Other disadvantages of using ferrite magnet material are that the ceramic-like material is very brittle and tends to chip. This feature is particularly undesirable in the well logging environment, where logging instruments are placed under enormous hydrostatic pressure and are subjected to severe mechanical shock. Ferrites also have low coercive force (Hc) which may lead to irreversible demagnetization, and ferrite loses its magnetization at a rate of about 0.2% per degree C. Temperatures in some wellbores can exceed surface temperatures by 100 to 150 degrees C. These temperatures reduce the permanent magnet material's residual magnetization (Br) by about 20% to 30% and can reduce the magnet material's coercive force (Hc) substantially, thereby leading to irreversible demagnetization of a permanent magnet made from ferrite.

Certain magnet materials have particular disadvantages when used in well logging applications. NMR magnetoacoustic ringing is known to be a particular concern due to high acoustic quality factor of ceramics. Alnico magnet materials have very low coercive force (Hc) which may lead to irreversible demagnetization. Both Alnico and Neodymium-Iron-Boron magnets have very poor temperature characteristics and therefore are not preferred for well logging tools.

Using resin-bonded Samarium-Cobalt or resin bonded Neodymium-Iron-Boron magnets is known in the art. For example, British patent application no. 2,141,236 filed by Clow et al on May 23, 1984 shows an NMR well logging instrument similar in configuration to the instrument shown in the Jackson et al '955 patent described earlier. The Clow et al '236 application states that the instrument uses resin-bonded Samarium-Cobalt magnets. The Clow et al '236 application does not describe any particular limitations on the structure or composition of the magnet material used in the instrument, and as a practical matter, the instrument described by Clow et al has never become commercially accepted primarily because excessive conductivity of the Samarium-Cobalt magnets distorts the RF magnetic field generated by the antenna. Using resin-bonded Samarium-Cobalt or resin bonded Neodymium-Iron-Boron magnets made according to processes known in the art has generally not proven suitable in commercially preferred types of NMR well logging apparatus, such as described in the Taicher et al '713 patent, because of the electrical conductivity of such magnets.

SUMMARY OF THE INVENTION

The invention is a nuclear magnetic resonance well logging apparatus, comprising an antenna for inducing a radio frequency magnetic field in earth formations surrounding the apparatus and for detecting nuclear magnetic resonance signals from the earth formations. In one embodiment of the invention, the antenna is a transversal dipole antenna. The apparatus includes a magnet for including a static magnetic field within the earth formations. The magnet is formed from a powdered, electrically conductive permanent magnet material. The grain size of the magnet material small enough with respect to the frequency of the radio frequency magnetic field to substantially prevent intragranular power loss of the radio frequency magnetic field. The magnet is assembled from electrically isolated blocks of the magnet material each having a thickness less than a skin depth of the radio frequency magnetic field within the magnet material. The boundaries between contiguous ones of the blocks are oriented to interrupt flow of eddy currents in the magnet resulting from the radio frequency magnetic field. In a preferred embodiment of the invention, the magnet material comprises powdered, epoxy resin-bonded Samarium-Cobalt.

DESCRIPTION OF THE PREFERRED EMBODIMENT

1. General Configuration of an NMR Well Logging Apparatus

Figure 1:
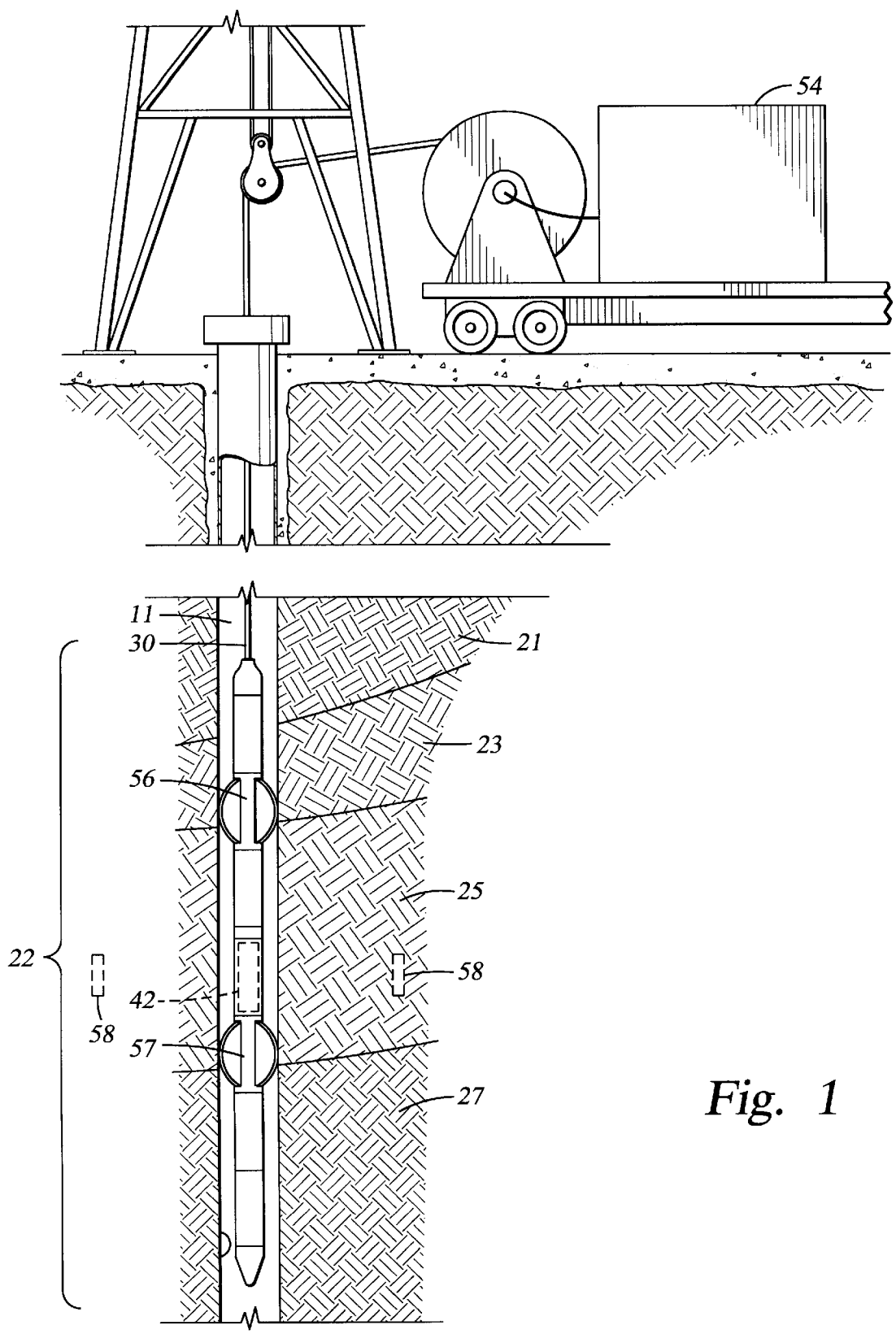
FIG. 1 shows a nuclear magnetic resonance (NMR) well logging apparatus disposed in a wellbore penetrating earth formations.

FIG. 1 shows a well logging apparatus (referred to as a "tool string" 22) disposed in a wellbore 11 drilled through earth formations 21, 23, 25, 27. The tool string 22 includes various sensors for measuring selected properties of the earth formations 21, 23, 25, 27 particularly within a predetermined volume of investigation 58, also referred to as the "sensitive volume". The tool string 22, which can include a nuclear magnetic resonance ("NMR") apparatus according to the invention, is typically lowered into the wellbore 11 by means of a winch-driven armored electrical cable 30 or similar conveyance known in the art. The NMR apparatus can be included in an NMR probe 42, comprising an antenna (not shown in FIG. 1), and a permanent magnet assembly (not shown separately in FIG. 1) made according to the invention forming part of the tool string 22. The tool string 22 can be connected, through the electrical cable 30, to surface equipment 54 including circuitry (not shown separately) for decoding and interpreting signals sent over the cable 30 from the tool string 22. Circuits for decoding and interpreting the signals sent by the tool string 22 over the cable 30 are well known in the art.

The tool string 22 including the NMR probe 42 is preferably centered within the wellbore 11 by means of a top centralizer 56 and a bottom centralizer 57 attached to the tool string 22 at axially spaced apart locations. The centralizers 56, 57 can be of types well known in the art such as bowsprings, or power operated "arms" such as shown in U.S. Pat. No. 4,614,250 issued to Panetta et al, for example. Other types of well logging sensors (not shown separately for clarity of the illustration in FIG. 1) may also form part of the tool string 22.

Figure 2A:
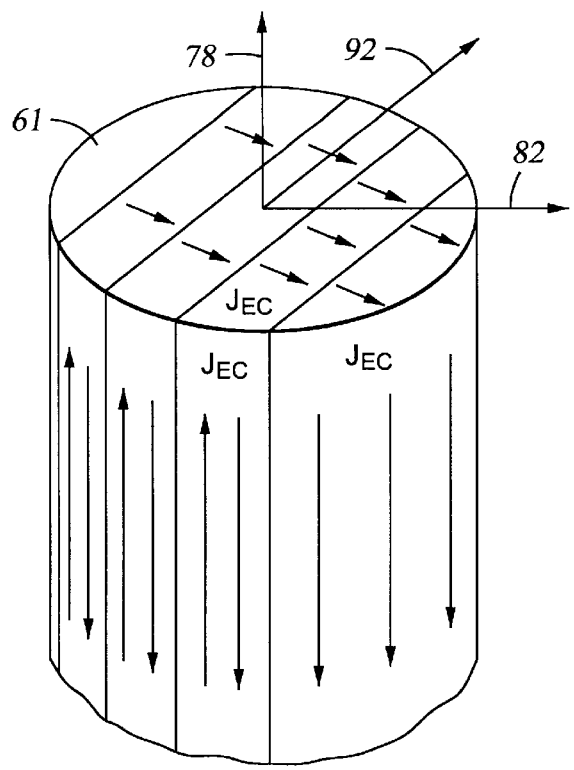
FIG. 2 shows an NMR probe with a transversal dipole antenna.
Figure 2B:
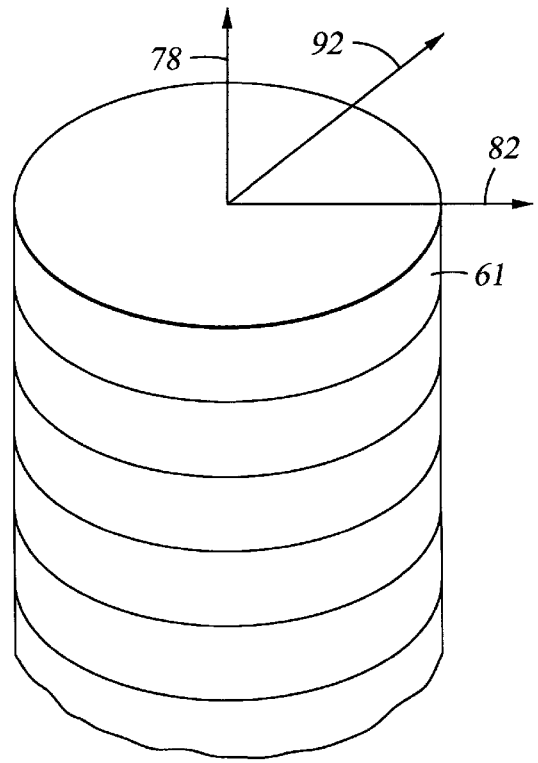

Referring now to FIG. 2, the NMR probe 42 portion of the tool string (22 in FIG. 1) is shown in a simplified manner. The NMR probe 42 includes a permanent magnet 61, which in this invention can be made from an electrically conductive magnet material. Particular electrically conductive materials from which the magnet 61 preferably is formed will be further explained. The probe 42 also can include an antenna, which in this embodiment can be a transverse dipole antenna 70. The magnet 61 in this embodiment of the invention can have substantially uniform magnetization along a longitudinal axis 78 and a magnetization direction 82 which is substantially perpendicular to the longitudinal axis 78. When radio frequency ("RF") power is passed through the antenna 70, it produces an RF magnetic field in the space outside the probe 42 (which includes the previously described earth formations 21, 23, 25, 27 in FIG. 1) and also inside the volume of the probe 42 itself where the permanent magnet 61 is located. Suitable electronic circuits for generating the RF power to pass through the antenna are well known in the art, as are circuits for measuring the magnitude of the NMR signals induced in the antenna 70. Suitable circuits are described for example, U.S. Pat. No. 4,710,713 to Taicher et al.

The RF magnetic field emanating from the antenna 70 would be homogeneous only if the magnet 61 were to be physically absent, or if the magnet 61 were substantially transparent to the RF magnetic field. A homogeneous RF magnetic field in the space occupied by the magnet 61 would correspond to a sinusoidal distribution, with respect to azimuthal direction about the longitudinal axis 78, of electric current density in the antenna 70. The RF magnetic field direction 92 for the transverse dipole antenna 70 shown in FIG. 2 is substantially perpendicular to the longitudinal axis 78 and is perpendicular to the magnetization direction 82 of the magnet 61. The geometry of the antenna 70 and the magnet 61 of the NMR probe 42 shown in FIG. 2 is used here to illustrate the principles underlying the invention. It is to be clearly understood that the principles of the invention as described herein may be extended to a variety of other antenna configurations and RF field configurations (for example, the RF field generated by a longitudinal dipole antenna) as well as other configurations for the magnet 61. Therefore the configuration of the antenna 70 and magnetization direction 82 of the magnet 61 described herein is not to be construed as a limitation the invention.

If the magnet 61 is made from an electrically conductive material, however, the RF magnetic field generated by the antenna 70 will induce eddy currents within the magnet 61 itself. These eddy currents would have two deleterious effects on the NMR probe 42 performance. First, some of the RF power would be absorbed in the magnet 61, which would reduce the quality factor ("Q") of the antenna 70. Second, the eddy currents themselves produce a secondary RF magnetic field which significantly distorts the RF field radiated by the antenna 70 within the volume of investigation (the sensitive volume 58 in FIG. 1). Both of these eddy current effects depend on the electrical conductivity of the magnet material, and on the geometries of both the magnet 61 and the antenna 70. These geometries in turn determine a particular eddy current flow configuration. The eddy current flow paths shown in FIG. 2 are for the particular configuration of the magnet 61 and the antenna 70 shown in FIG. 2.

2. Construction of a Magnet for the NMR Apparatus Which Has Appropriate Magnetic Properties and Negligible Eddy Current Effect As explained in the Background section herein, magnet materials exist, such as resin-bonded Samarium-Cobalt which would have more suitable magnetic and mechanical properties for NMR well logging applications than do the ferrite materials used in typical NMR well logging instruments. However, these more suitable magnet materials are substantially electrically conductive, and so if used unmodified in an NMR well logging instrument would cause distortion of the RF magnetic field, as well as reductions of the signal-to-noise ratio as a result of RF power loss in the magnet, as previously explained herein.

Resin-bonded magnets formed from such conductive magnet materials, as explained in the Background section herein, can have their bulk electrical conductivity reduced by increasing the fractional amount of non-conductive resin with respect to the amount of magnetic material in the finished magnet. However, if the fractional amount of the magnetic material in the finished magnet is too small, the resulting magnet would have magnetic properties no better than those of ferrite, which is substantially non-conductive. The invention seeks to maintain the desirable mechanical and magnetic properties of the conductive magnet materials in a finished resin-bonded magnet, while having suitable electrical conductance properties for use in an NMR well logging instrument.

Figure 3A:
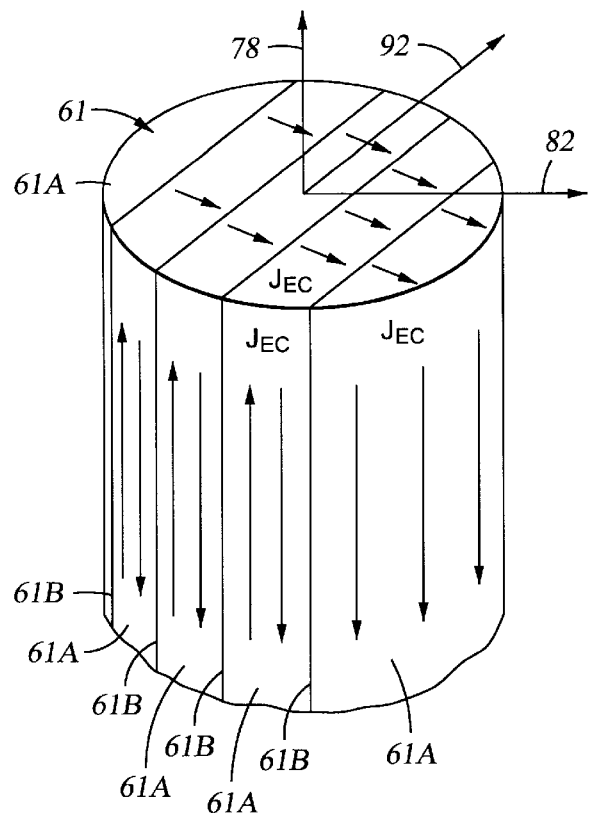
FIGS. 3A and 3B show a magnet in the NMR probe of FIG. 2. segmented in a way relevant for use with the transversal dipole antenna

FIG. 3A illustrates part of the principle of the invention. The permanent magnet 61, can be formed, in a manner which will be further explained, from resin-bonded, electrically conductive powdered magnet material such as Samarium-Cobalt. The resin bonded powdered magnet material can be formed into individual "blocks" which are assembled to form the complete permanent magnet 61 as shown in FIG. 3A. The blocks, shown generally at 61A, can have substantially planar faces, primarily for ease of assembly into the completed magnet 61. The planar faces between adjoining blocks 61A preferably have thin sheets of electrically insulating material ("inserts") 61B positioned therebetween, so that the blocks 61A are substantially electrically isolated from each other.

It is generally sufficient that the insulating inserts 61B located between adjacent blocks 61A are more or less parallel to a plane which is parallel to the principal RF magnetic field direction 92. The insulating inserts 61B between the blocks 61A shown in FIG. 3A are substantially parallel to the plane formed by the longitudinal axis 78 and the RF magnetic field direction 92 so as to interrupt paths of eddy currents which would otherwise flow within the magnet 61. This orientation of the inserts 61B is particularly suitable for the arrangement of the magnet 61 and the transversal dipole antenna 70 as shown in FIG. 2. Other orientations for the inserts 61B suitable for other particular orientations of the static and RF magnetic fields will be explained later herein.

The purpose of assembling the magnet 61 from the electrically isolated blocks 61A is to reduce the effects of the eddy currents which are induced in the magnet 61 as a result of the RF magnetic field. The effect on the eddy current losses by such a sectioning of the permanent magnet 61 may be calculated by the following analysis. The specific RF power absorption, P, (power absorption per unit volume) due to eddy currents flowing within an infinite-dimension, planar "sheet" may be calculated according to the equation:

$$P=(\omega^2 \cdot B^2 \cdot a^2/2\rho)\cdot(1/w^3)\cdot[\sin h(w)-\sin (w)]/[\cos h(w)-\cos (w)] \quad (1)$$

where $\delta$ equals $\omega\mu_0/\rho$; $w=a\cdot(\delta/2)^{1/2}$; $\omega$ and B represent the circular (angular) frequency and the magnetic flux density of the RF magnetic field, respectively. $\rho$ represents the electrical resistivity of the "sheet" material, and $\alpha$ represents the thickness of the individual "sheet". The "sheet" represented in equation (1) would correspond to each one of the individual blocks 61A in FIG. 3A. The calculation for specific power absorption from eddy currents is described, for example, W. R. Smythe, *Static and Dynamic Electricity*, McGraw-Hill Book Company, Inc., New York (1950).

Figure 4:
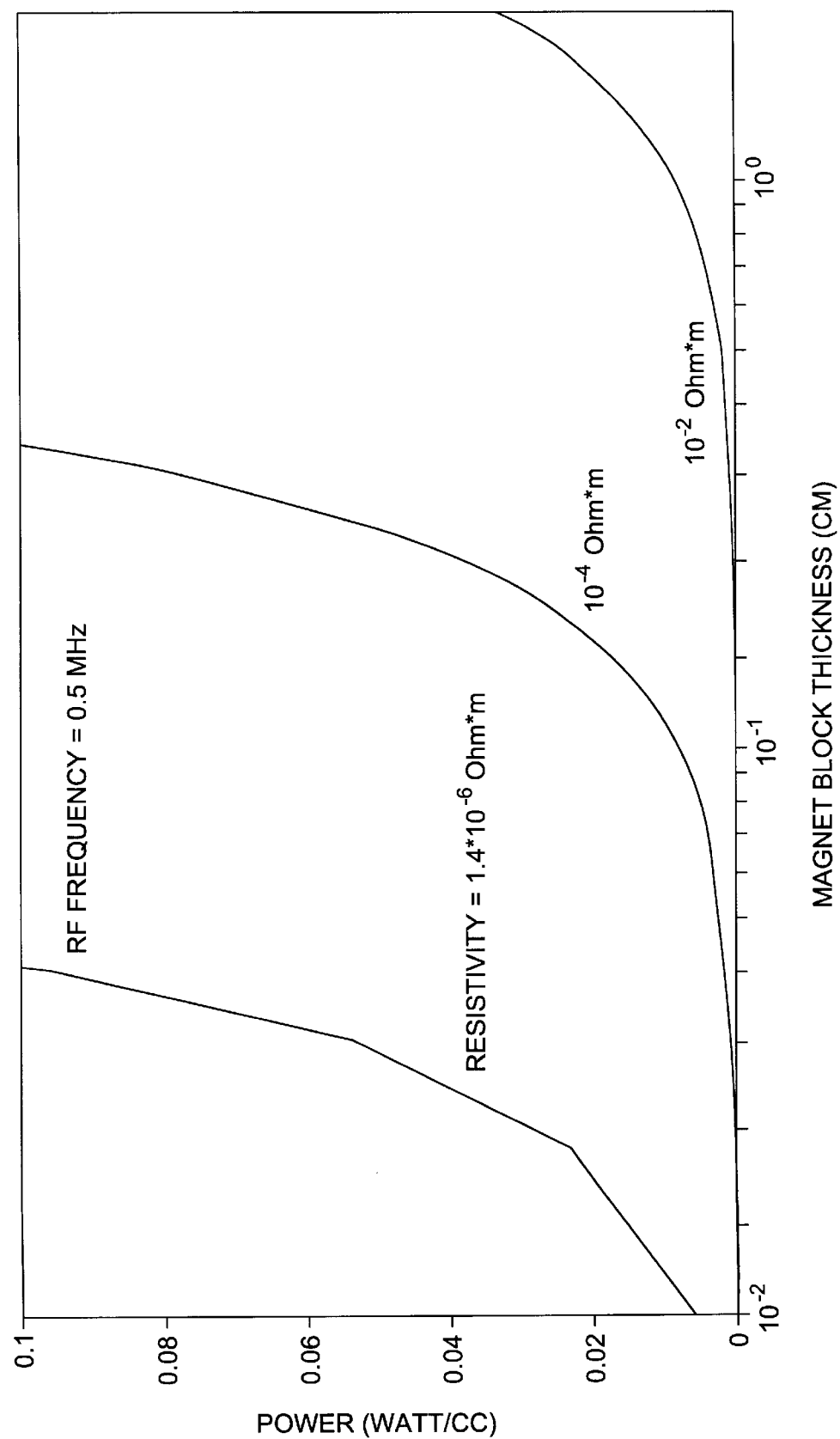
FIG. 4 shows a graph of correspondence between magnet block thickness for the magnet of the invention with respect to RF power absorption.

FIG. 4 shows a graph of the specific power absorption with respect to the block ("sheet") thickness $\alpha$. The specific power absorption shown by the graphs in FIG. 4 is calculated for an RF magnetic field having a frequency, f, of $\omega/2\pi=0.5$ Mhz, an RF magnetic field flux density, B, equal to 1 mT, and using three different resistivities for the magnet material: $\rho=1.4\times10^{-6}$ Ohm-m; $\rho=1\times10^{-4}$ Ohm-m; and $\rho=1\times 10^{-2}$ Ohm-m. The first value of resistivity of the magnet material, $\rho$, corresponds to sintered, neodymium-iron-boron magnets. The higher values of resistivity correspond to the resin-bonded, powdered rare-earth (Samarium-Cobalt) magnets, which will be described later in more detail.

It should be noted that the specific power absorption of any particular block (61A in FIG. 3A) reaches a maximum value, and then decreases with respect to increasing thickness, $\alpha$, of the block (61A in FIG. 3A). This inflection occurs at values beyond the limits of the vertical axis of the graph in FIG. 4. This power absorptive behavior corresponds to the magnitude of the skin effect, wherein the power absorption takes place only within a certain thickness layer (the so-called "skin-depth layer") along the exterior surface of any one of the blocks (61A in FIG. 3A). As the thickness of the individual blocks 61A exceeds the skin depth of the material from which the blocks 61A are made, the specific power absorption will decrease because eddy currents do not flow within the bulk of the block material away from the skin-depth layer. Strong skin effect causes very strong distortion of the RF magnetic field outside the logging instrument (and therefore in the earth formations) and therefore should be avoided. As a practical matter, the skin depth for the magnet materials used in the invention, for the RF magnetic frequencies typically used in the NMR probe, is typically much more than the overall dimensions of the magnet (61 in FIG. 3A).

For any value of specific power loss in a magnet material where the skin depth is greater than the block thickness, equation (1) shows that the overall power loss in any given block is generally related to the square of the block thickness. By assembling the magnet from relatively thin blocks, the effect of eddy current is reduced. Theoretically, the overall power loss in the magnet 61 could be made negligible by making the blocks very thin. It could be difficult and expensive to create a finished magnet from a large number of such thin "laminated" sections. Therefore the invention seeks to define a thickness for the blocks which will provide acceptable NMR probe performance without having an unduly large number of blocks in the finished magnet 61.

As a practical matter, the blocks 61A in the magnet 61 of the invention can have a block thickness, $\alpha$, selected to provide a minimum predetermined value of quality factor ("Q) for the antenna (70 in FIG. 2) for any particular conductivity value of the magnet material and RF magnetic field frequency. The procedure for selecting the block thickness can be explained as follows. Referring one again to FIG. 3A, surface eddy currents, $j_{ec}$, at adjacent block 61A surfaces compensate each other for their effect on the RF magnetic field radiated externally to each individual block 61A. The total effect of the eddy currents, $j_{ec}$, on the RF magnetic field outside the magnet 61 would be about the same as the effect on the magnetic field for a one-piece magnet having eddy currents distributed only along the magnet's 61 surface (see FIG. 2). This surface current produces a secondary RF magnetic field which exactly cancels the external field (B) within the volume of the magnet 61 (as strong skin effect takes place) and almost cancels the RF field within the sensitive volume (58 in FIG. 1). Given that a minimum acceptable quality factor, Q, of the antenna 70 can be defined by the system designer, the maximum thickness, $\alpha$, may be estimated for a particular antenna and magnet geometry. For the magnet 61 shown in FIG. 3A the total RF power absorption, $P_{ab}$, within the magnet 61 can be calculated from equation (1) by the expression:

$$P_{ab} = \pi \cdot R_m^2 \cdot L_a \cdot P \tag{2}$$

where $R_m$ and $L_a$ are the radius of the magnet 61 and the length of the antenna (70 in FIG. 2), respectively. The quality factor, Q, is defined as the ratio of the maximum magnetic energy, $W_{mag}$, to the total absorbed energy, $W_{ab}$. $W_{ab} = P_{ab} \times T$, where T represents the period of the RF magnetic field:

$$Q = W_{mag}/P_{ab} \cdot T \tag{3}$$

The maximum magnetic energy can be calculated by the expression:

$$W_{mag} = \int (B^2/2\mu_0) dv \tag{4}$$

where the integral is taken over the whole space. For the case of a sinusoidal distribution, with respect to azimuth, of the current density, $j_a$, in the antenna (70 in FIG. 2) the expression for the total magnetic energy reduces to:

$$W_{mag} = (1/\mu_0)\pi \cdot R_m^2 \cdot L_a B^2 \tag{5}$$

Figure 5:
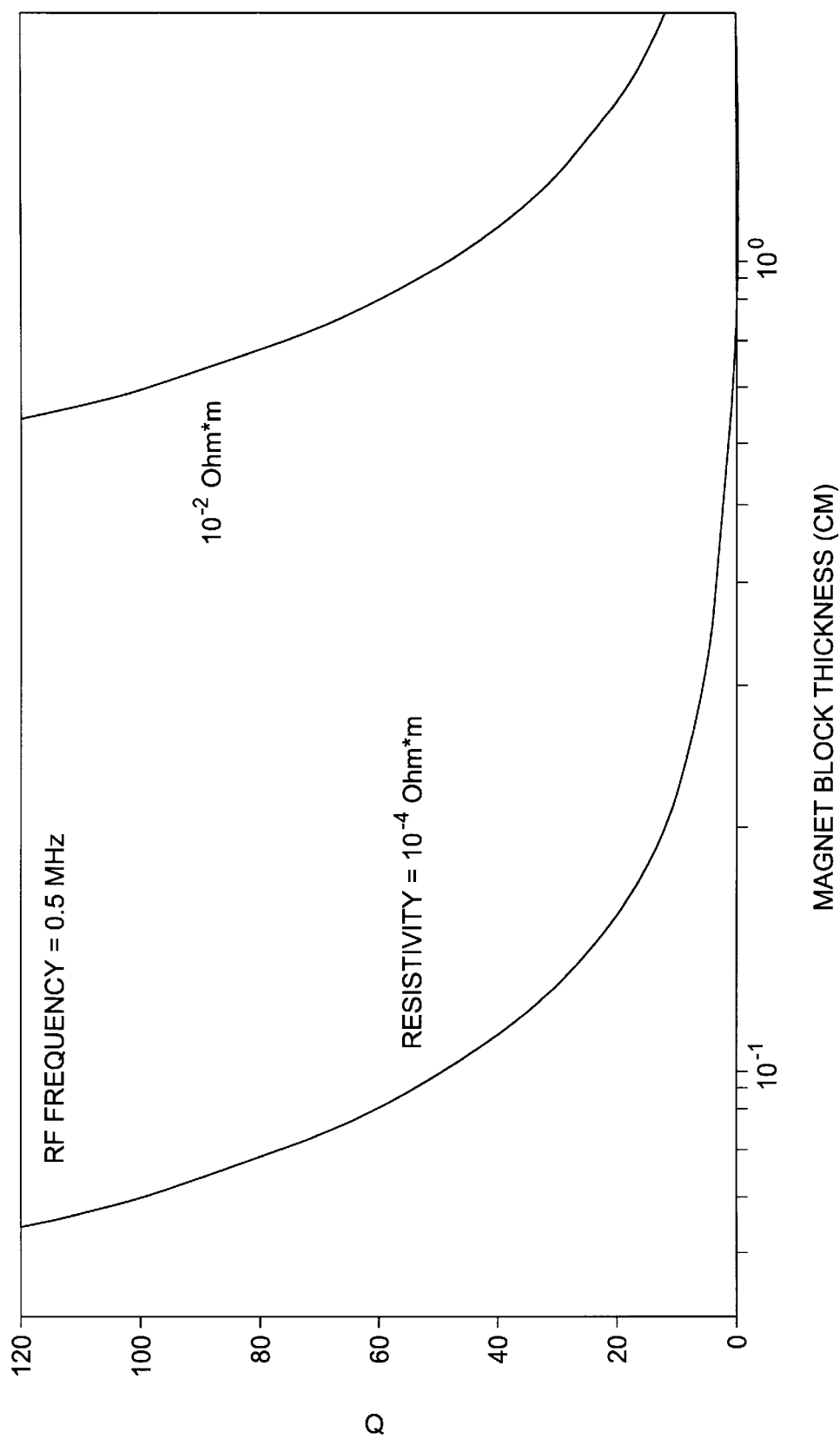
FIG. 5 shows a graph of correspondence between the magnet block thickness for the magnet of the invention with respect to the quality factor (Q) of the antenna.

The quality factor, Q, with respect to the block thickness, α, is shown graphically in FIG. 5. A practical value of Q for the NMR probe 42 can be about 20. For Q of about 20, α should be about 0.2 cm and 1.5 cm, respectively, for a magnet material resistivity of $\rho = 10^{-4}$ Ohm-m, and $\rho = 10^{-2}$ Ohm-m. The frequency of the RF magnetic field used in these calculations is 0.5 MHz. Appropriate block thicknesses may be readily calculated for other RF magnetic field frequencies and for other conductivity values of material used for the magnet 61.

As previously explained, conductive magnet materials having resistivity, ρ, in the range from about $10^{-4}$ to $10^{-2}$ Ohm-m may be formed into a type of resin-bonded permanent magnet. This type of magnet can be made, for example, from $SmCo_5$, $Sm_2Co_{17}$ (Samarium-Cobalt) or Nd-Fe-B (Neodymium-Iron-Boron) magnetic material powders. Nonconductive bonding material such as epoxy or other polymeric resin provides reduction of the overall inter-grain electric conductivity and increases the macroscopic (overall bulk) resistivity of the magnet made from such materials.

The particle size in typical powdered magnet materials generally varies within a range from about 1μ to 1 mm. The particle sizes for the resin-bonded magnets known in the art are intentionally distributed over this size range in order to improve the "packing" of the powder grains, in order to increase the overall density and remanence magnetization of the finished magnet. See for example, "New Resin-Bonded Sm-Co Magnet Having High Energy Product (SAM)", Proceedings of the Fourth International Workshop on Rare Earth-Cobalt Permanent Magnets and Their Applications, Hakone National Park, Japan (1979). For the larger particles in this size range, however, the RF power absorption inside the individual particles may not be negligible, thus producing microscopic (within the permanent magnet material particles themselves) eddy current losses. In the invention, to ensure that the particles themselves do not contribute to RF power loss, the particle size is intentionally limited to that which will substantially eliminate intragranular RF power losses. The maximum acceptable particle size for any given RF magnetic field frequency can be estimated by the following analysis.

A single grain of the magnet material powder can be represented by a conductive sphere having a radius, R, having an electrical resistivity, ρ, and having a magnetic permeability μ=1. This is a good approximation for permanent magnets having initial magnetic susceptibility, χ, much less than 1. The expression for the RF power absorbed in magnet powder grains represented as conductive spheres is (e. g. see the W. R. Smythe, reference, supra):

$$P_g = (3\pi\omega^2 R^5 B^2/\rho) \{(u/2)[\sin h(u) + \sin (u)] - \cos h(u) + \cos (u)\}/p^2 R^4 [\cos h(u) - \cos (u)] \tag{6}$$

where $\delta = \omega\mu_0/\rho$; $u = 2\delta^{1/2}R$; ω and B represent the angular frequency and magnetic flux density of the RF magnetic field, ρ represents electrical resistivity of the magnetic material, and R represents the grain (sphere) radius. The overall power loss per unit volume, P, of a material made from grains having uniform size equal to sphere radius, R, can then be expressed as:

$$P = 3p_f P_g/4\pi R^3, \tag{7}$$

where $p_f$ represents the volume packing factor of the finished resin-bonded magnet material made from the grains having radius R.

Figure 6:
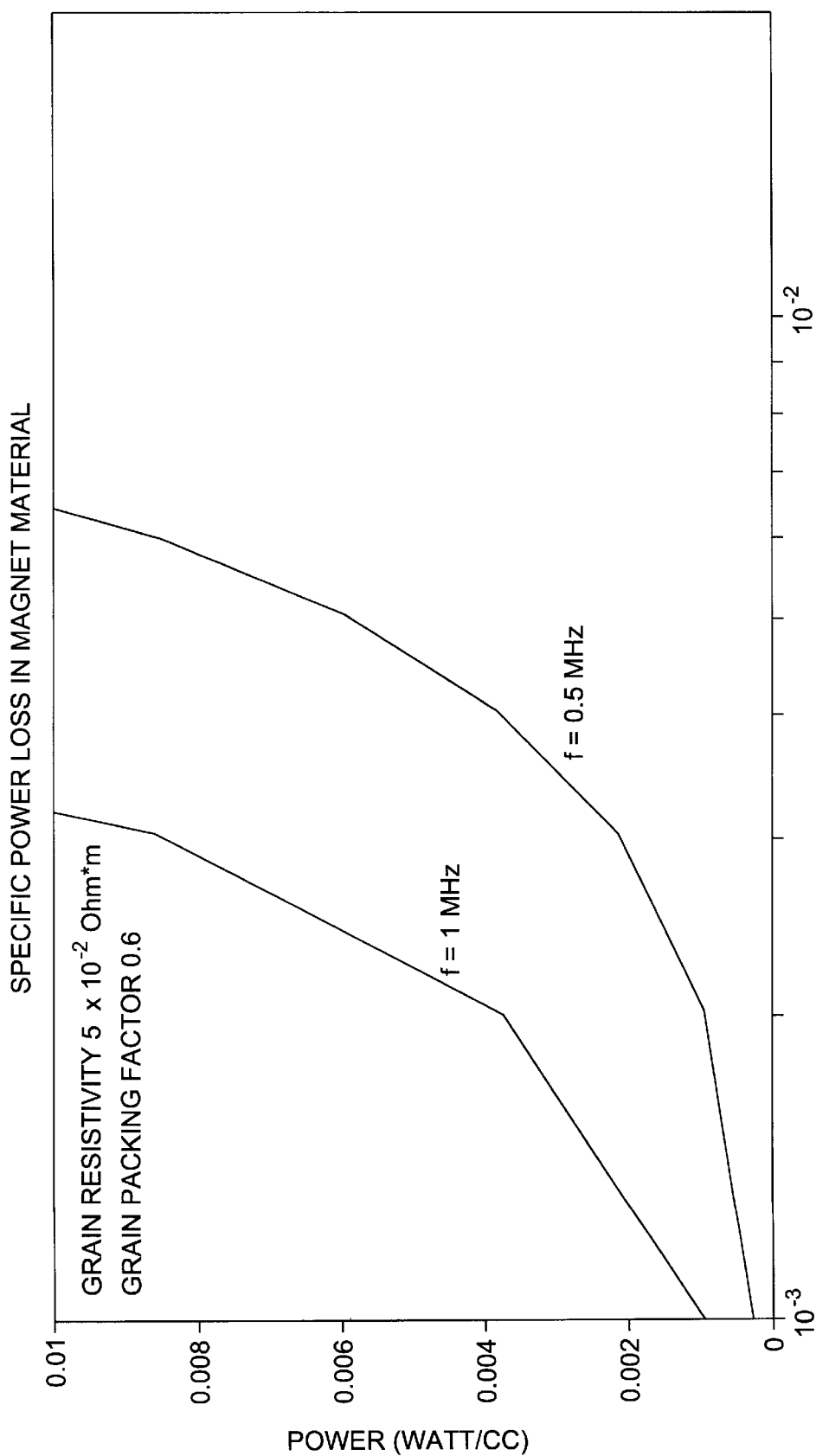
FIG. 6 shows a graph of particle size dependence of RF power absorption for a particulate magnet material.

FIG. 6 shows the dependence of the specific power absorption with respect to magnet material grain radius, R, for an RF magnetic field flux density, B, equal to 1 mT, an electrical resistivity of the grains, ρ, equal to $5 \times 10^{-7}$ Ohm-m (which is a typical value for Sm-Co magnet alloys), and $p_f$ equal to 0.6. Comparison with the data for specific power loss as shown in FIG. 4 indicates that at a frequency of 0.5 MHz the intragranular power loss is negligible (defined as being about one order of magnitude less than the specific power losses shown in FIG. 4) if the grain size is less than about 50μ. The maximum acceptable grain size in the powdered magnet material can be readily calculated for other frequencies of the RF magnetic field by the expressions shown herein.

For reasons related to achieving an appropriate coercivity, and other magnetic properties, the size of the magnetic material particles may actually be limited to those much smaller than is suggested by the data shown in FIG. 6. A feasibility experiment for making magnets using controlled particle sizes according to the previous specification used an epoxy-resin bonded magnet made from $SmCo_5$ particles in a size range from 4 to 10μ. The macroscopic resistivity of the resulting magnet was about $1 \times 10^{-2}$ Ohm-m and the remanence magnetization, Br, was about 0.45 T.

Figure 3B:
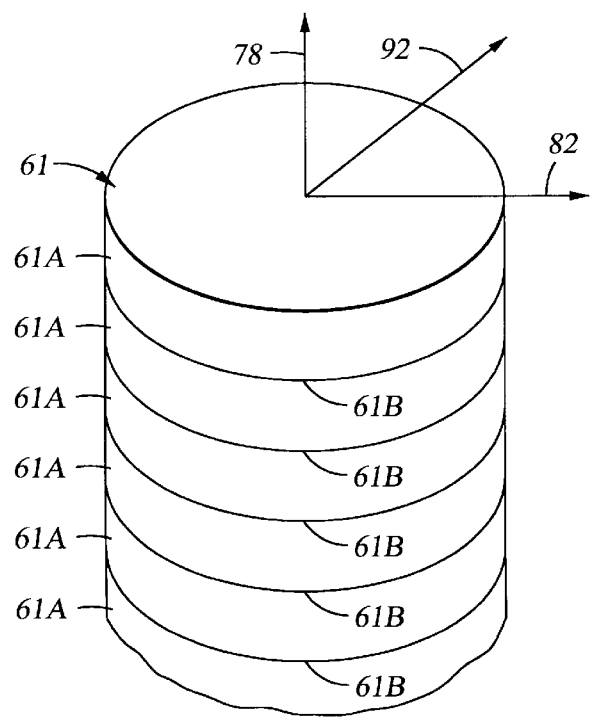

As was previously explained, the orientation of the boundaries between the individual magnet blocks should be such as to interrupt flow of eddy currents in the magnet. An alternative embodiment of the magnet 61 with segmenting appropriate for the transversal dipole NMR antenna (70 in FIG. 2) is shown in FIG. 3B. The magnet 61 is segmented in the form of cylindrical-disk shaped blocks 61A having substantially planar faces and insulating inserts 61B substantially perpendicular to the longitudinal axis 78. If the magnet block 61A thickness, α, is small compared to the magnet 61 diameter, the calculations presented previously herein are still valid, since the geometry can be also approximated by an infinite sheet with an RF field parallel to the sheet plane.

Figure 3C:
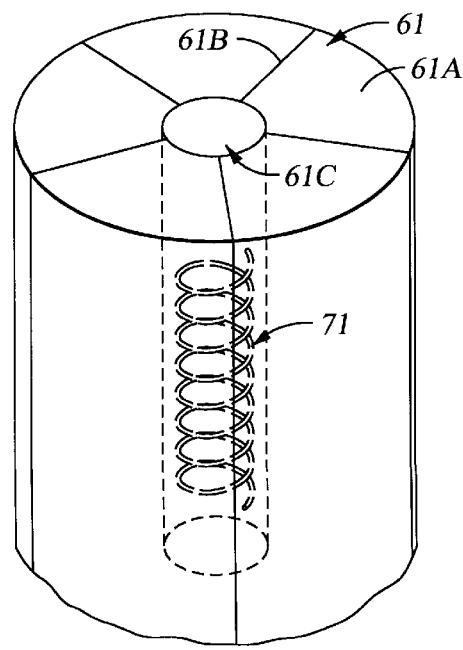
FIG. 3C shows a magnet suitable for use with a longitudinal dipole antenna.

It should be apparent to those skilled in the art that similar analysis may be performed for a longitudinal dipole antenna. The longitudinal RF magnetic field of such an antenna produces eddy currents flowing around the longitudinal axis in a plane perpendicular to the longitudinal axis 78. Any planar insulating inserts which are parallel to the longitudinal axis 78 will provide effective segmenting of the magnet 61. One alternative configuration of segmenting the magnet for a longitudinal dipole antenna is shown in FIG. 3C. The magnet 61 in FIG. 3C includes magnet blocks 61A having insulating inserts 61B between adjacent blocks 61A. The insulating insets 61B should be substantially in planes parallel to the longitudinal axis 78 and along lines radially outward from the longitudinal axis 78 so as to interrupt the paths of eddy currents which would otherwise flow in the magnet 61 as a result of the RF magnetic field induced by a longitudinal dipole antenna 71. In the embodiment shown in FIG. 3C, the longitudinal dipole antenna 71 can be disposed in a hole 61C in the center of the magnet 61, but this is not intended as an exclusive representation of how the longitudinal dipole antenna 71 may be disposed with respect to the magnet 61.

It should be noted that the field radiated by the longitudinal dipole antenna 71 is not exactly along the longitudinal axis 78 direction in practice. There is also a transversal (radial) component of the RF magnetic field at the longitudinal ends of such an antenna. It can be understood in this case that segmenting which interrupts paths of eddy current flowing in planes perpendicular to the longitudinal axis 78 will modify the original eddy current flow paths in a way that eddy currents will flow in paths along the longitudinal axis 78 near the ends of the longitudinal dipole antenna 71. A combination of segmenting with insulating inserts parallel to (shown at 61B) and perpendicular to (not shown in FIG. 3C) the longitudinal axis 78 may improve the efficiency of segmenting in this case.

Other modes of segmenting of the magnet 61 may be devised so as to interrupt paths of eddy currents induced by any other selected configuration of RF magnetic field.

DESCRIPTION OF ALTERNATIVE EMBODIMENTS

As explained in the description of the first embodiment of the invention, the overall electrical conductivity of a resin-bonded, powdered magnet including conductive magnetic material powder is related to the proportion of powdered magnetic material in the finished magnet. In the first embodiment of the invention, the magnetic powder proportion and resulting conductivity of the finished magnet is not controlled. Eddy current losses in the magnet are reduced by assembling the magnet from individual pieces (the blocks 61A in FIG. 3A) oriented to interrupt eddy currents flowing in the magnet. The thickness of any one of the blocks (61A in FIG. 3A) is limited to that which provides a minimum acceptable Q factor for the antenna, given the conductivity of the finished magnet and the frequency of the RF magnetic field. Equations for calculating the maximum thickness are shown in the description of the first embodiment of the invention.

In the first embodiment of the invention, the finished magnet was made from magnet material having a proportion of powdered magnetic material intended to preserve the greatest possible remanence magnetization consistent with the other requirements for the finished magnet. Reducing the proportion of powdered magnetic material in a resin-bonded magnet, of course, does reduce the overall magnetization of the finished magnet. As previously explained, reducing the proportion of powdered magnetic material can result in a finished magnet having remanence magnetization less than a similar ferrite magnet, which is substantially non-conductive. It may still be desirable, however, to use resin-bonded magnet material to provide a finished magnet hacving reduced magnetic strength instead of ferrite magnet materials because the resin-bonded magnet materials using conductive powders such as Samarium-cobalt have the advantages of better thermal stability, and better resistance to mechanical failure as compared with ferrite magnet materials.

Consequently, in this embodiment of the invention the magnet (61 in FIG. 3A) can be formed from a single piece of resin-bonded magnet material, as described earlier herein. In this embodiment of the invention, however, the conductivity of the overall magnet material can be reduced, by reducing the proportion of powdered magnetic material in the finished magnet to a level which for the dimensions of the finished magnet will provide a minimum acceptable Q value for the antenna. The calculations for determining the conductivity of the magnet material with respect to the dimensions of the finished magnet to provide a particular value of Q for the antenna are described in the first embodiment of the invention, and are shown graphically in FIGS. 4–6.

In this embodiment of the invention the same limitations apply as to the maximum grain size of the powdered magnetic material as for the first embodiment of the invention. For example, for an RF magnetic field frequency of 0.5 MHZ, a maximum grain size of 50 microns for the powdered Samarium-Cobalt magnetic material will substantially prevent intragranular power loss in the finished magnet (61 in FIG. 3A).

Those skilled in the art will be able to devise other embodiments of the invention described herein which do not depart from the spirit of the invention. The embodiments shown herein are merely illustrative of the inventive concept and should not be interpreted as limiting the scope of the invention. Rather, the scope of the invention should be limited only by the claims which follow.

What is claimed is:

1. A nuclear magnetic resonance apparatus, comprising:
   an antenna for inducing a radio frequency magnetic field in materials to be analyzed and for detecting nuclear magnetic resonance signals from said materials; and
   a magnet for inducing a static magnetic field in said materials, said magnet formed from an electrically conductive permanent magnet material, said magnet assembled from electrically isolated blocks where boundaries between adjacent ones of said blocks are oriented to substantially interrupt flow of eddy currents induced in said magnet by said radio frequency field and wherein said blocks each have a thickness calculated to provide a predetermined minimum value of quality factor for said antenna.

2. The apparatus as defined in claim 1 wherein said eddy currents are induced by said radio frequency magnetic field.

3. The apparatus as defined in claim 1 wherein said electrically conductive permanent magnet material comprises powder having a maximum particle size with respect to a frequency of said radio frequency magnetic field so as to substantially prevent intragranular power loss of said radio frequency magnetic field.

4. The apparatus as defined in claim 1 wherein said electrically conductive magnet material comprises a powder bonded by a non-conductive material comprising polymeric resin.

5. The apparatus as defined in claim 1 wherein said electrically conductive material comprises Samarium-Cobalt.

6. The apparatus as defined in claim 1 wherein said electrically conductive magnet material comprises Neodymium-Iron-Boron.

7. The apparatus as defined in claim 1 wherein said antenna comprises a transversal dipole antenna disposed on an exterior surface of said magnet, and said boundaries are substantially parallel to said longitudinal axis and perpendicular to a principal magnetic field direction of said antenna.

8. The apparatus as defined in claim 1 wherein said antenna comprises a transversal dipole antenna disposed on an exterior surface of said magnet, and said boundaries are substantially perpendicular to said longitudinal axis.

9. The apparatus as defined in claim 1 wherein said antenna comprises a longitudinal dipole antenna, and said boundaries are substantially parallel to said longitudinal axis and extend radially outward from said longitudinal axis.

10. A nuclear magnetic resonance well logging apparatus, comprising:

an antenna for inducing a radio frequency magnetic field in earth formations surrounding said apparatus and for detecting nuclear magnetic resonance signals from said earth formations; and a magnet for inducing a static magnetic field within said earth formations, said magnet formed from an electrically conductive permanent magnet material, said magnet material having a maximum particle size with respect to a frequency of said radio frequency magnetic field to substantially prevent intragranular power loss of said radio frequency magnetic field, said magnet assembled from electrically isolated blocks of said magnet material where boundaries between adjacent ones of said blocks are oriented to substantially interrupt flow of eddy currents in said magnet.

11. The apparatus as defined in claim 10 wherein said eddy currents are induced by said radio frequency magnetic field.

12. The apparatus as defined in claim 10 wherein each of said blocks has a thickness calculated to provide a minimum value of quality factor for said antenna.

13. The well logging apparatus as defined in claim 10 wherein said electrically conductive magnet material comprises powdered magnetic material bonded by a nonconductive material comprising polymeric resin.

14. The well logging apparatus as defined in claim 10 wherein said electrically conductive magnet material comprises Samarium-Cobalt.

15. The well logging apparatus as defined in claim 10 wherein said electrically conductive magnet material comprises Neodymium-Iron-Boron.

16. The well logging apparatus as defined in claim 10 wherein said magnet comprises a cylinder having substantially uniform magnetization along a longitudinal axis of said cylinder and a magnetization direction substantially perpendicular to said longitudinal axis, said antenna comprises a transversal dipole antenna disposed on an exterior surface of said magnet, and said boundaries are substantially parallel to said longitudinal axis and substantially perpendicular to a principal magnetic field direction of said antenna.

17. The well logging apparatus as defined in claim 10 wherein said magnet comprises a cylinder having substantially uniform magnetization along a longitudinal axis of said cylinder and a magnetization direction substantially perpendicular to said longitudinal axis, said antenna comprises a transversal dipole antenna disposed on an exterior surface of said magnet, and said boundaries are substantially perpendicular to said longitudinal axis.

18. The well logging apparatus as defined in claim 10 wherein said magnet comprises a cylinder having substantially uniform magnetization along a longitudinal axis of said cylinder and a magnetization direction substantially perpendicular to said longitudinal axis, said antenna comprises a longitudinal dipole antenna, and said boundaries are substantially parallel to said longitudinal axis and extend substantially radially outward from said longitudinal axis.

19. A nuclear magnetic resonance sensing apparatus, comprising:

an antenna for inducing a radio frequency magnetic field in materials to be analyzed and for detecting nuclear magnetic resonance signals from said materials; and a magnet for inducing a static magnetic field within said materials, said magnet formed from a powdered, electrically conductive magnetic material and a non-conductive bonding agent, said powdered magnetic material having a maximum grain size to substantially prevent intragranular power loss of said radio frequency magnetic field.

20. The apparatus as defined in claim 19 wherein said powdered magnetic material comprises Samarium-Cobalt.

21. The apparatus as defined in claim 19 wherein said maximum grain size is about 50 microns corresponding to a frequency of said radio frequency magnetic field of about 0.5 MHz.

22. The apparatus as defined in claim 19 wherein said powdered magnetic material comprises Neodymium-Iron-Boron.

23. The apparatus as defined in claim 19 wherein said bonding agent comprises a polymeric resin.

24. The apparatus as defined in claim 19 wherein a proportion of said powdered, electrically conductive magnetic material in said magnet is selected to provide a predetermined electrical conductivity of said magnet, whereby a predetermined value of quality factor for said antenna is determined.

* * * * *